United States Patent [19]

Gaffar

[11] 4,342,857
[45] Aug. 3, 1982

[54] ANTIGINGIVITIS COMPOSITION COMPRISING VINYL PHOSPHONIC ACID/VINYL PHOSPHONYL FLUORIDE COPOLYMER

[75] Inventor: Abdul Gaffar, Somerset, N.J.

[73] Assignee: Colgate-Palmolive Company, New York, N.Y.

[21] Appl. No.: 221,582

[22] Filed: Dec. 31, 1980

[51] Int. Cl.³ .................... C08F 8/12; C08F 214/18; C08F 230/02
[52] U.S. Cl. .................................. 525/326.4; 424/52; 525/383; 526/278; 526/242

[58] Field of Search ................ 525/331, 383; 526/242, 526/278

[56] References Cited

U.S. PATENT DOCUMENTS 3,297,663  1/1967  Herbst et al. ...................... 526/278
3,320,115  5/1967  Reid et al. ........................... 525/383

Primary Examiner—Harry Wong, Jr.
Attorney, Agent, or Firm—Herbert S. Sylvester; Murray M. Grill; Robert L. Stone

[57] ABSTRACT

A novel vinyl phosphonic acid/vinyl phosphonyl fluoride copolymer, and oral compositions containing the same, are disclosed having antigingivitis activity.

6 Claims, No Drawings

ANTIGINGIVITIS COMPOSITION COMPRISING VINYL PHOSPHONIC ACID/VINYL PHOSPHONYL FLUORIDE COPOLYMER

This invention relates to non-antibacterial agents and oral compositions which promote oral hygiene, and especially to such agents and compositions for treating, controlling or inhibiting gingivitis which is characterized by such symptoms as inflammation, bleeding, recession, and/or swelling of the gums. Types of gingivitis include afunctional gingivitis, gingivitis marginal and cotton-roll gingivitis. Gingivitis leads to periodontitis.

The gums are seriously harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes.

*Actinomyces viscosus*, a gram positive rod, has been identified as implicated in the etiology of gingivitis Loeche et al "Bacteriology of human experimental gingivitis: effects of plaque and gingivitis sores," Infection and Immunity 21, 830–839 (1978). This organism attaches to tooth surfaces to form the dental plaque.

A multitude of materials have been previously proposed and employed for controlling plaque, calculus, tartar, caries, halitosis, and gingivitis, but none have been entirely satisfactory. For example, some of such materials have been found to be unstable in the presence of the anionic surface active agents generally present in conventional oral preparations. A number of such materials such as the cationic quaternary ammonium agents exert an antibacterial function which undesirably tends to disrupt or destroy the normal microflora of the mouth and/or the digestive system.

It is an object of this invention to provide antigingivitis materials, agents, oral compositions and/or methods which will not be subject to one or more of the above deficiencies. Other objects and advantages will appear as the description proceeds.

The attainment of the above objects is made possible by my discovery of a novel material or agent, more particularly a copolymer, which interferes with or inhibits the attachment of *Actinomyces viscosus* to saliva coated hydroxyapatitie (HAP) beads. This is a reliable indication that the agent would interfere with the attachment of the organism to tooth surfaces, should reduce plaque, and hence reduce or inhibit gingivitis. Such antigingivitis activity has in fact been corroborated by an in vivo test on beagles as more fully discussed below.

In accordance with certain of its aspects, this invention relates to a novel water soluble copolymer which is an effective antigingivitis agent, such copolymer being composed predominantly of:

(A) units having the molecular configuration of units derived from vinylphosphonic acid, and (B) units derived from vinyl phosphonyl fluoride, the ratio of (A) units to (B) units ranging from about 2:1 to about 25:1.

The (A) units in the copolymer may be depicted as having the structural formula:

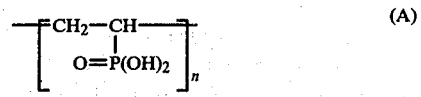

n being a numerical value representing the number of (A) units. The (B) units may be depicted as having the structural formula:

m being a numerical value representing the number of (B) units in the copolymer.

It will be understood that the (A) and (B) units are randomly distributed in the copolymer molecule and that the copolymer may also contain minor proportions, i.e. less than 50 wt. %, preferably less than about 10 wt. %, more preferably less than about 5 wt. %, of units derived from other ethylenically unsaturated monomers which, in type and amount, are nontoxic and do not interfere with the desired water soluble and antigingivitis activities of the copolymer. Other such monomers may, for example, include olefins such as ethylene, propylene, isopropylene, butylene and isobutylene, vinyl lower alkyl ethers such as vinyl methyl, ethyl and isobutyl ethers, alpha, beta unsaturated carboxylic acids and their lower alkyl and substituted lower alkyl esters such as acrylic, methacrylic, aconitic, maleic and fumaric acids and their methyl, ethyl isobutyl and dimethylaminoethyl esters, allyl alcohol and acetate, vinyl and vinylidene halides, vinyl lower alkanoic acid esters such as vinyl acetate and butyrate, acrylamide and methacrylamide and N-lower alkyland N,N-dilower alkyl substituted derivatives thereof, other vinyl phosphonyl halides, and the like.

The copolymers of this invention should preferably have a number average molecular weight of about 2,000, to about 50,000, more preferably about 3,500 to about 16,000, and are prepared by polymerizing a mixture of vinyl phosphonyl chloride, as precursor of the (A) units, and vinyl phosphonyl fluoride under substantially anhydrous conditions in the presence of a free radical catalyst, and then mixing the resulting copolymer with water to hydrolytically convert the vinyl phosphonyl chloride units in the copolymer to vinyl phosphonic acid (A) units.

The mixture to be polymerized should contain proportions of vinyl phosphonyl chloride and vinyl phosphonyl fluoride within the (A):(B) unit ratios defined above, and may optionally contain minor non-interfering amounts of other nontoxic non-interfering ethylenically unsaturated monomers as also disclosed hereinabove. The mixture is subjected to well known free radical initiated addition polymerization conditions.

Any compound which generates free radicals under the conditions of reaction can be used as a polymerization initiator in the present reaction. Preferred types are peroxy compounds and azonitriles. Exemplary peroxy compounds are dibenzoyl peroxide, dilauroyl peroxide, dimethyl peroxide, diethyl peroxide, di-t-butyl peroxide, dioctadecyl peroxide, t-butyl peroxy pivalate, disuccinoyl peroxide, urea peroxide, peracetic and perbenzoic acids, alkyl and dialkylboron peroxides and alkali metal persulfates, perborates, and percarbonates, alone or in combination with a reducing agent Exemplary azonitriles are
1,1′-azodicyclohexanecarbonitrile,
a,a′-azobis(a-cyclopropylpropionitrile),
a,a′-azobis(isobutyronitrile)(AIBN),
a,a′-azobis(a,γ-dimethylvaleronitrile),
a,a′-azobis(a-methyleneanthronitrile),
a,a′-azobis(a-phenylpropionitrile,
a,a′-azobis(a-cyclohexylpropionitrile),
a,a′-azobis(a-methyl-γ-carboxybutyronitrile),
disodium γ,γ′-azobis(γcyanovalerate),
1,1′-azodicamphanecarbonitrile, etc.

Particularly preferred for use herein are those initiators or catalysts which are lyophilic, i.e. monomer soluble or water insoluble, such as AIBN, and dilauroyl, dibenzoyl and di-t-butyl peroxides. The amount of initiator to be employed in any particular instance is readily determinable by routine experimentation, being influenced by the particular monomer mixture, temperature of reaction, results desired, etc. Generally, at least about 0.005% to about 10% of the initiator based on the weight of the monomer mixture define practical extremes, about 1% to about 8% more usual. Elevated temperatures are generally employed such as about 40° C. to about 125° C., preferably about 50° C. to about 85° C. for a time sufficient to yield a copolymer having the desired molecular weight. In some instances an organic solvent medium may be employed to promote better contact between the monomers and better control of the reaction.

Following completion of the polymerization of the mixture containing the vinyl phosphonyl chloride and fluoride monomers, the reaction medium is mixed with water to hydrolyze the chloride to OH. This is preferably conducted at low temperatures, e.g. below about 10° C. The resulting copolymer of the invention is in free acid form and may desirably be converted to salt form by treatment with any orally acceptable cation-providing base such as alkali metal (e.g. sodium or potassium), ammonium, $C_{1-18}$ mono-, di- and tri-substituted ammonium, (e.g. alkanol substituted such as mono-, di- and tri-ethanolammonium), organic amines, etc. It will be understood that the salt form of the copolymer is the equivalent of the free acid form and that the term "water soluble" applicable to both forms is inclusive of readily water dispersible forms thereof in the usual use concentrations.

In accordance with other of its aspects, this invention relates to an oral composition adapted to inhibit symptoms of gingivitis comprising an oral (orally acceptable) vehicle and an effective antigingivitis amount of the above-described water soluble copolymer of this invention.

The concentration of these copolymer antigingivitis agents in oral compositions can range widely, typically upwards of about 0.01% by weight with no upper limit except as dictated by cost or incompatibility with the vehicle. Generally, concentrations of about 0.01% to about 10.0%, preferably about 0.1% to about 8.0%, more preferably about 0.5% to about 5.0% by weight are utilized. Oral compositions which in the ordinary course of usage could be accidentally ingested preferably contain concentrations in the lower portions of the foregoing ranges.

In certain highly preferred forms of the invention, the oral composition may be substantially liquid such as a mouthwash or rinse. Such preparations generally contain a humectant and the vehicle is typically a water-alcohol mixture. Generally, the ratio of water to alcohol is in the range of from about 1:1 to about 20:1 preferably from 3:1 to 20:1 and most preferably about 17.3, by weight. The total amount of water-alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a lower pH without substantially decalcifying dental enamel.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 $cm^2/gm.$, silica gel, complex amorphorus alkali metal aluminosilicate, hydrated alumina, dicalcium phosphate.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, fourth Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 10 to about 99% by weight of the oral preparation. Preferably, it is present in amounts ranging from about 10 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antigingivitis agent and polishing material should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients are polyethlene glycol and polypropylene glycol. Also advantageous are liquid mixtures of water, glycerine and sorbitol.

In clear gels where the refractive index is an important consideration, about 3–30% by weight of water, 0 to about 80% by weight of glycerin, and about 20–80% by weight of sorbitol is preferably employed. A gelling agent, such as natural or synthetic gums or gumlike materials, typically Irish moss, sodium carboxymethylcellulose, methyl cellulose, hydroxyethyl cellulose, gum tragacanth, polyvinylpyrrolidone, starch, and preferably hydroxypropyl methyl cellulose and the Carbopols (e.g. 934,940 and 941), etcetera is usually present in toothpaste in an amount up to about 10% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31–38, and such suitable nonionic surfactants in col. 8, lines 30–68 and col. 9, lines 1–12, which passages are incorporated herein by reference thereto.

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, Ca fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013 by weight, of fluoride.

Various other materials may be incorporated in the oral preparations of this invention, subject to the above. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed, also subject to the above. Examples of suitable flavoring constituents are flavoring oils, e.g., oils of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, sodium cyclamate, perillartine, APM (aspartylphenylalanine, methyl ester) and saccharin. Suitably, flavor and sweetening agents may together comprise from about 0.1 to 5% or more of the preparation.

In the practice of this invention an oral composition according to this invention such as a mouthwash or toothpaste containing the antigingivitis agent in an orally acceptable vehicle may be prepared by unifying the components in conventional manner, and applied to the gingiva and teeth regularly, from about 1 to 3 times daily, at a pH of about 4.5 to about 9, generally about 5.5 to about 8.5, preferably about 6 to about 8.

The following examples are further illustrative of the nature of this invention but it is understood that the invention is not limited thereto. All amounts and proportions referred to herein and in the appended claims are by weight, and temperatures are in degrees C. unless otherwise indicated.

EXAMPLE I (SYNTHESIS AND POLYMERIZATION)

Vinylphosphonylchloride [$C_2H_3P(O)Cl_2$]

Vinyl-bis($\beta$-chloroethyl)phosphonate (93.0 g, 0.4 moles) and 0.680 g copper (I) chloride were heated to 135° C.±5° in a 500 ml 3-necked flask fitted with a mechanical stirrer, thermometer and claisen head. The claisen head was used to facilitate the addition of the phosphorus pentachloride as well as the removal of 1,2-dichloroethane and $POCl_3$. After allowing the intial mixture to come to 135° C.±5° C., phosphorus pentachloride (167.0 g, 0.80 moles) was introduced portionwise at a rate consistent with a slow but steady evolution of gaseous by-products. After the addition of the phosphorus pentachloride was complete and the reaction visually subsided, the mixture was allowed to cool to room temperature and was vacuum distilled to give 42.05 g (72.5%) $\eta_D^{20}$=1.4800 (lit $\eta_D^{20}$=1.4808) bP 67°-69° C./21 mm. After 2 hr. the water and HCl were removed under vacuum and the residual vinylphosphonic acid was titrated, giving two equivalent end points and an equivalent weight of 108.

Vinylphosphonylfluoride [$C_2H_3P(O)F_2$]

Vinylphosphonylchloride (24.0 g, 0.165 moles) was mechanically stirred with anhydrous zinc fluoride (18 g, 0.174 moles) in a 50-ml 2-neck flask connected to a water aspirator through a dry ice trap. An aspirator vacuum (<50 torr) was applied and the reaction mixture was warmed to just above 30° C. After approximately two minutes at 30° C. a vigorous reaction ensued. After the reaction subsided the temperature of the pot was raised to 60° C. while still maintaining an aspirator vacuum. When no further material was being collected the contents of the trap were removed, warmed to room temperature and distilled at atmospheric pressure to give 15.0 g (0.134 moles, 81% yield) of the difluoride bp 95°-96° C. (lit 95° C.). This material was further characterized by a strong P-F band at 955 cm$^{-1}$ in its infrared spectrum as well as the following fluorine analysis data:

| | Calc for $C_2H_3POF_2$ | |
|---|---|---|
| | Theory | Found |
| % F | 33.93 | 34.0 |

COPOLYMERIZATION OF VINYLPHOSPHONYLCHLORIDE AND VINYLPHOSPHONYLFLUORIDE

Three copolymers were prepared in the following ratios of vinylphosphonylchloride/vinylphosphonylfluoride: 4/1, 9/1, and 19/1. The following description of the preparation of the 9/1 copolymer is identical to the procedures used in the preparation of the 4/1 and 19/1 copolymers.

Vinylphosphonylfluoride (3.36 g, 0.030 moles) was mechanically stirred with vinylphosphonylchloride (39.15 g, 0.270 moles) and azobisisobutyronitrile (ABIN) (1.656 g, 0.009 moles, 3 mole %) in a 100-ml resin pot under a nitrogen atmosphere. The reaction mixture was heated to 50° C.±1° C. for 2 hr. After 2 h the temperature was increased to 70° C. and maintained at this temperature for 18 hr. The resultant orange viscous polymer was cooled to room temperature at which point stirring was extremely difficult. Hydrolysis was accomplished by adding excess water dropwise at below 10° C. The excess water and HCl were removed under high vacuum to yield a white solid. Titration of the white solid gave two equivalent end points (somewhat hazy owing to a polyelectrolyte effect) with the second end point at pH=11.0. The polymer was then titrated to pH=11.0 with aqueous sodium hydroxide and dried under high vacuum at 30°-35° C. for 96 hr. Fluorine analysis gave the following data for all three copolymers: (as sodium salts)

| Copolymer | % F - Theory | % F - Found |
|---|---|---|
| 4/1 (molar) | 5.28 | 4.60 |
| 9/1 | 2.56 | 2.56 |
| 19/1 | 1.27 | 1.27 |

Phosphorus analysis gave the following data: (as sodium salts)

| Copolymer | % P - Theory | % P - Found |
|---|---|---|
| 4/1 | 21.5 | 20.0 |
| 9/1 | 20.9 | 18.8 |
| 19/1 | 17.67 | 16.2 |

Viscosity data were obtained for these three copolymers in water (as the sodium salts). These data are shown in the following table along with approximate molecular weights.*

*Calculations were made using the constants for polyacrylic acid since no constants are known for this polymer system.

| Copolymer | Intrinsic Viscosity | $\overline{MW}_n$ |
|---|---|---|
| 4/1 | 0.256 | 15,200 |
| 9/1 | 0.242 | 13,900 |
| 19/1 | 0.112 | 5,800 |

EXAMPLE II

Effects of copolymer of vinyl phosphonic acid and vinyl phosphonylfluoride (VPAVPF) on the attachment of *Actinomyces viscous* to saliva treated hydroxyapatite (HAP) beads.

Reaction mixture (1.0 ml) contained 5×10$^7$ $^3$H-thymidine-labeled bacteria and 30 mg saliva treated hydroxyapatite beads in 0.05 MKCl containing 1 mM Cacl$_2$, 1 mM PO$_4$ and 0.1 mM MgCl$_2$. The assay was run in duplicate. The mixture was continuously shaken at room temperature for 2 hours. The beads were allowed to settle for 1 min. and the supernatant which contained unabsorbed cells was removed. The radiation activity was measured via Liquid scintillation counter. Portions of known number of $^3$H Labelled cells were counted in a similar manner so that counts per minute could be related to bacterial cell numbers. Control bacterial suspensions were incubated with HAP beads and counted similarly to correct for cell loss to absorption to tubes.

TABLE I

Effects of pretreating saliva-coated HAP beads with VPAVPF for one hour.

| | A. Viscosus (LY7) # of cells absorbed (× 10⁶) per 30 mg. HAP | % Relative to Buffer |
|---|---|---|
| Buffered KCl | 39.7 | 100 |
| 1% VPAVPF (4/1) | 14.6 | 36 |
| 0.1% VPAVPF (4/1) | 31.9 | 80 |
| 0.01% VPAVPF (4/1) | 35.1 | 88 |
| Buffered KCl | 39.7 | 100 |
| 1% VPAVPF (9/1) | 9.9 | 24 |
| 0.1% VPAVPF (9/1) | 33.2 | 83 |
| 0.01% VPAVPF (9/1) | 34.3 | 86 |
| Buffered KCl | 22.6 | 100 |
| 1% VPAVPF (19/1) | 0.99 | 4 |
| 0.1% VPAVPF (19/1) | 19.6 | 84 |

TABLE II

Effects of pretreating A. Viscosus with VPAVPF for one hour.

| | A. Viscosus (LY7) # of cells absorbed (× 10⁶) per 30 mg. HAP | % Relative to Buffer |
|---|---|---|
| Buffered KCl | 54.7 | 100 |
| 1% VPAVPF (4/1) | 36.3 | 66 |
| Buffered KCl | 54.7 | 100 |
| 1% VPAVPF (9/1) | 44.1 | 80 |
| 0.1% VPAVPF (9/1) | 52.1 | 95 |
| Buffered KCl | 22.1 | 100 |
| 1% VPAVPF (19/1) | 0.96 | 4 |
| 0.1% VPAVPF (19/1) | 17.8 | 81 |
| 0.01% VPAVPF (19/1) | 20.2 | 91 |

TABLES I and II above show that the VPAVPF copolymers of this invention are effective in inhibiting bacterial absorption on saliva treated HAP beads when applied first to either the HAP beads or the bacterial cells.

EXAMPLE III

Invivo Test on Beagles

This study in 20 beagles evaluates the effects of 0.5% VPAVPF copolymer (19.1) on gingivitis in beagles. Placebo rinse served as a control. The dogs were given complete prophylaxis to remove soft and hard dental deposits. A disclosing solution was used to insure the complete removal of the deposits. The beagles were then kept on soft diet for a period of six weeks. This permitted the development of gingivitis. The gingival inflammation was assessed by the method of Loe and Silness; Acta Odonto Logica Scandinavica 21: 551:555, (1963).

After the baseline gingivitis, group I (10 dogs) were treated with the placebo rinse, while the group II was treated with the rinse containing copolymer. The treatment was done twice daily 5 days per week. The effects were evaluated after 3, 6 and 8 weeks of treatment. The study was double blind and undercode. That is, neither the evaluator nor the people involved in treatment knew the assignments of rinses to the respective groups.

TABLE III

| | | RESULTS Original Index/Teeth | Treatment Period | | |
|---|---|---|---|---|---|
| Mouthrinse | Group | Prior to Treatment | 3 wks | 6 wks | 8 wks |
| Placebo | I | 1.45 ± 0.14* | 1.5 ± 0.15 | 1.5 ± 0.14 | 1.9 ± 0.17 |
| 0.5% VPAVPF | II | 1.46 ± 0.17 | 1.1 ± 0.14 | 1.3 ± 0.21 | 1.4 ± 0.23 |

*Standard Deviation

The statistical analysis of the data by Kendall Test* showed that there were no differences among the groups prior to the start of the treatment regime suggesting that the groups were well balanced. At 3, 6 and 8 weeks the copolymer significantly reduced gingivitis compared to the placebo. This difference was significant at the 95 percent interval.

*Kendall Independent Test.

The following examples of oral (mouthwash and toothpaste) formulations are further illustrative of this invention. In these examples, the VPAVPF is a 4/1, 9/1 or 19/1 copolymer as described above.

EXAMPLE IV

| | Wt. Percent |
|---|---|
| Glycerin | 25.0 |
| Carboxymethylcellulose | 1.3 |
| Sodium benzoate | 0.5 |
| Saccharin | 0.2 |
| Silica | 30.0 |
| Solium laurylsulfate | 1.5 |
| Flavor | 1.0 |
| VPAVPF Copolymer | 3.0 |
| Water to make | 100.0 |

EXAMPLE V

| | Wt. Percent |
|---|---|
| Ethanol | 10.0 |
| Polyethyleneglycol 600 | 10.0 |
| Saccharin | 0.03 |
| Flavor | 0.2 |
| VPAVPF Copolymer | 1.0 |
| Water to make | 100.0 |

This invention has been described with respect to preferred embodiments and it will be understood that modifications and variations thereof obvious to those skilled in the art are to be included within the spirit and preview of this application and the scope of the appended claims.

What is claimed is:

1. A water soluble copolymer composed predominantly of:

(A) units having the molecular configuration

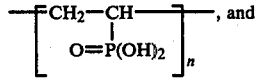, and (B) units having the molecular configuration

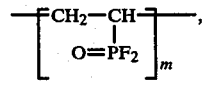, the ratio of (A) units (n) to (B) units (m) ranging from about 2:1 to about 25:1.

2. A copolymer according to claim 1 having a number average molecular weight of about 2,000 to about 50,000.

3. A copolymer according to claim 1 wherein the ratio of (A) units to (B) units is about 4:1.

4. A copolymer according to claim 1 wherein the ratio of (A) units to (B) units is about 9:1.

5. A copolymer according to claim 1 wherein the ratio of (A) units to (B) units is about 19:1.

6. A method of preparing a copolymer as defined in any of claims 1 to 5 comprising polymerizing a mixture of vinyl phosphonyl chloride, as precursor of the (A) units, and vinyl phosphonyl fluoride under substantially anhydrous conditions in the presence of a free radical catalyst, and then mixing the resulting copolymer with water to hydrolytically convert the vinyl phosphonyl chloride units in the copolymer to vinyl phosphonic acid (A) units.

* * * * *